United States Patent [19]
Felix

[11] Patent Number: 6,062,074
[45] Date of Patent: May 16, 2000

[54] METHOD FOR DETECTING PERIODIC DEFECTS IN A TEST MATERIAL MOVED LONGITUDINALLY

[75] Inventor: Ernst Felix, Uster, Switzerland

[73] Assignee: Zellweger Luwa AG, Uster, Switzerland

[21] Appl. No.: 09/206,240

[22] Filed: Dec. 7, 1998

[30] Foreign Application Priority Data

Dec. 17, 1997 [CH] Switzerland ............... 2891/97

[51] Int. Cl.⁷ ................................. G01N 27/00
[52] U.S. Cl. ............................................. 73/160
[58] Field of Search ............. 73/160, 159; 19/239; 57/265

[56] References Cited

U.S. PATENT DOCUMENTS

| | | |
|---|---|---|
| 4,058,962 | 11/1977 | Spescha et al. . |
| 4,152,931 | 5/1979 | Mannhart ..................... 73/160 |
| 4,982,600 | 1/1991 | Kiso et al. . |
| 5,592,849 | 1/1997 | Nakade et al. . |

FOREIGN PATENT DOCUMENTS

| | | |
|---|---|---|
| 0 358 236 | 3/1990 | European Pat. Off. . |
| 0 594 220 | 4/1994 | European Pat. Off. . |
| 2 338 884 | 8/1977 | France . |
| 27 50 152 | 9/1978 | Germany . |
| 43 35 262 | 4/1994 | Germany . |
| 89/00215 | 1/1989 | WIPO . |

*Primary Examiner*—Robert Raevis
*Attorney, Agent, or Firm*—Burns, Doane, Swecker & Mathis

[57] ABSTRACT

The invention relates to a method and apparatus for detecting periodic defects in a test material moved longitudinally. In order to enable periodic defects in elongate test material moved longitudinally to be continuously detected with little expenditure, at least two measurements of a parameter which follow one another at a comparatively short interval (W/2) are to be carried out at time intervals (T1, T2, T3).

8 Claims, 1 Drawing Sheet

METHOD FOR DETECTING PERIODIC DEFECTS IN A TEST MATERIAL MOVED LONGITUDINALLY

FIELD OF THE INVENTION

The invention relates to a method and apparatus for detecting periodic defects in a test material moved longitudinally. It is concerned particularly with detecting, during such yarn production operations as those of spinning machines which involve large numbers of production paths functioning in parallel with one another, which of the production paths may be mavericks in the sense of producing periodic defects in the long lengths of material being produced.

BACKGROUND OF THE INVENTION

Faults in production machines such as, e.g. ring spinning machines, repeatedly give rise to periodic cross-sectional fluctuations in the test material, such as, e.g. in yarns. Front cylinders running out of true in ring spinning machines are particularly responsible for such cross-sectional fluctuations. These result in the known, disturbing moire' effects in the finished products. An eccentricity of a front cylinder of just, e.g. 0.1 mm, has a very disturbing effect. Although most front cylinders are sufficiently true-running, it is not uncommon to find so-called mavericks, i.e, front cylinders which give rise to considerable cross-sectional fluctuations in the yarn.

However it is very difficult, for example in ring spinning machines, to detect production stations which give rise to defects in the yarn or test material. It is in most cases hardly possible to visually detect any eccentricity. It would in principle be possible to carry out measurements with a dial gauge. However such measurements are so complicated that they are confined to just individual cases or research.

In practice only the finished yarns are subjected to quality control in the spinning mill. This has until now been carried out in the laboratory by means of random samples. In this case, however, it would be extremely valuable to detect the so-called mavericks, i.e. the inadequately running production stations. Yet this is only possible with full-scale control, not just with random samples. However a spinning mill has tens of thousands of production stations. Routine quality control directly at each production station is therefore absolutely unrealistic on account of the large number of production stations. There are no existing methods or devices which are able to meet the above requirement in any form, even just to a certain degree.

SUMMARY OF THE INVENTION

An object of the invention is to provide a method and apparatus with which periodic defects in elongate test material moved longitudinally can be continuously detected with little expenditure.

In a method according to the invention, groups of measurements are made with respect to a test material (e.g., a yarn) parameter to be examined for periodic fluctuations of a type which might be caused by irregularities in components of the production equipment. The parameter which is measured is preferably the diameter or the mass of the test material. There are only small number (e.g., two) measurements in each groups of measurements and these measurements follow one another at a comparatively short interval. On the other hand, the groups of measurements take place at widely spaced times during the production day.

The apparatus comprises at least two sensors which are disposed at a spacing from one another such that they can travel on a track in front of production units of a machine. These may be of a type disclosed in Swiss Application No. 2890/97, filed Dec. 17, 1998, and in its corresponding United States patent application being filed concurrently herewith under attorney docket number 030705-153, the entire disclosure such applications being incorporated herein by reference. Together the sensors form a so-called traveling sensor with at least two measuring members which each detect the cross section and/or diameter of the test material at each production station in succession as the traveling sensor travels past.

The above-mentioned measuring members or sensors are at a spacing from one another which, taking account of the traveling speed of the traveling sensor and the production speed of the test material, corresponds approximately to one half-wavelength of the sought period and/or an integer multiple thereof. The measurement results of the measuring members in each case obtained from the same production or spinning station are correlated and stored in association with each spinning station, thereby enabling periodic fluctuations in the yarn to be detected. An at least approximate detection of the yarn cross section and/or yarn diameter takes place in the sensors or measuring members when the traveling sensor travels past the production stations, the spacing of the measuring members in the traveling sensor being of a magnitude such that the traveling sensor has covered a distance corresponding approximately to the spacing of the measuring members in the time in which a length which corresponds approximately to one half-wavelength of the corresponding period and/or the integer multiple thereof has been produced in the yarn. Electronic means are also provided to evaluate and store the measurement results.

The advantages achieved by the invention lie in particular in the fact that it enables practically complete control of all production stations to be achieved without having to associate a particular control element with each production station.

BRIEF DESCRIPTION OF THE DRAWINGS

The invention is illustrated in detail in the following on the basis of an example and with reference to the accompanying figures, in which.

DETAILED DESCRIPTION OF PREFERRED EMBODIMENTS

Figure 1:
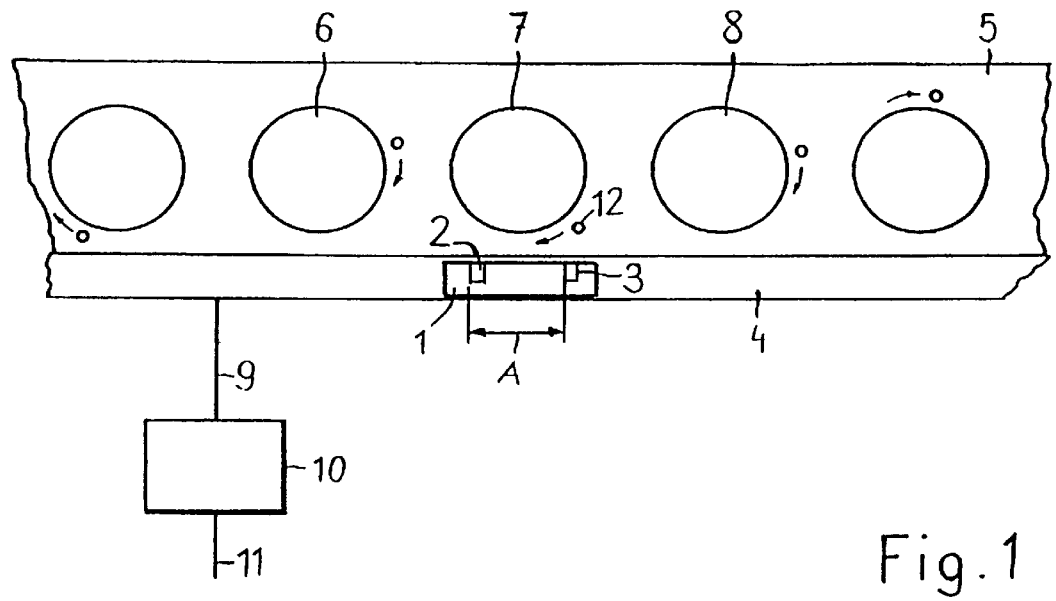
FIG. 1 is a diagrammatic view of an apparatus according to the invention.

FIG. 1 shows in diagrammatic form a traveling sensor 1 with two measuring members 2 and 3 which is disposed such that it can travel on a track or bar 4 along a ring rail 5 with the spinning stations 6, 7 and 8 as production stations. The measuring members 2, 3 are connected via a line 9 to an evaluation unit 10 with an output 11. Each measuring member 2, 3 in the traveling sensor detects the yarn 12 rotating at the spinning station upon traveling past and delivers a signal which is at least approximately proportional to the yarn diameter or yarn cross section or the mass of the yarn or test material.

Periodic fluctuations due to defective front cylinders in the drafting systems are usually of particular interest where ring spinning machines are concerned. The spacing A of the measuring members must in these cases be of a magnitude such that the traveling sensor 1 covers a distance corresponding to the spacing A of the measuring members 2, 3 in the time in which yarn of a length corresponding approximately to half the circumference of the front cylinders is produced.

If, e.g. the circumference of the front cylinders is 10 cm (top and bottom cylinders are generally approximately of the same size), i.e. half the circumference is 5 cm, and the production speed 16 cm per second, then yarn of a length which corresponds to half the circumference of the front cylinder has been produced in $5/16$ seconds. If, on the other hand, the speed of the traveling sensor is, e.g. 20 cm per second, it covers a distance of 6.25 cm in $5/16$ seconds. The spacing A of the two measuring members 2, 3 in the traveling sensor 1 should then be 6.25 cm.

However the spacing need not be particularly accurate for the designated purpose. The usual fluctuations in the production speed, which in theory would always necessitate a different spacing, do not have a disturbing effect.

In order to obtain information on periodic defects, the signals or values from both measuring members must be evaluated or correlated in a suitable manner.

Figure 2:
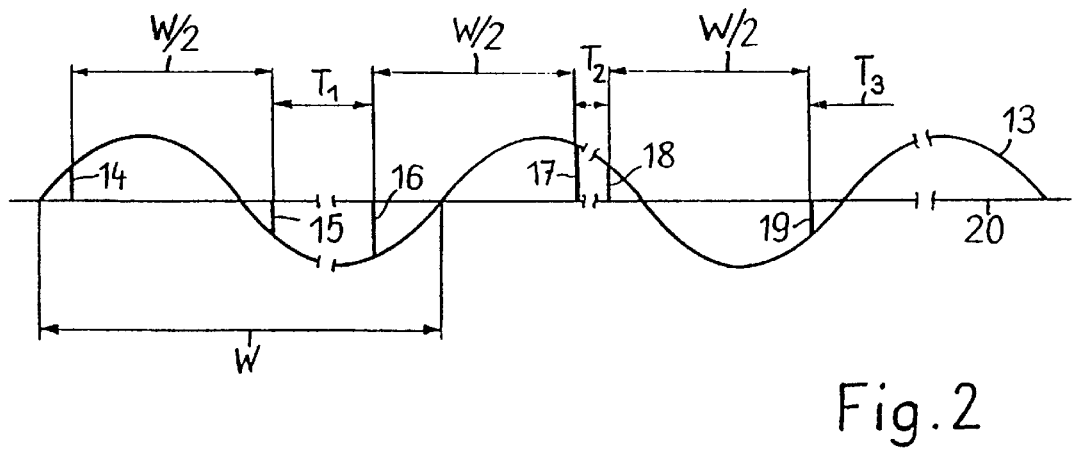
FIG. 2 is a diagrammatic view of a method according to the invention.

In order to provide a better understanding of an example of how the signals of the two measuring members 2, 3 may be mathematically correlated, a hypothetical case will now be explained on the basis of FIG. 2. The yarn in this case has just one purely periodic fluctuation with a wavelength W corresponding to the circumference U of a front cylinder. This fluctuation is designated and represented by 13 in FIG. 2. In accordance with an embodiment according to the invention, the two measuring members 2, 3 undertake at time intervals T1, T2, T3, etc. at least two measurements of a parameter which follow one another at a comparatively short interval W/2. The spacing A in the traveling sensor is such that a pair of values 14–15, 16–17 and 18–19 is always recorded at an interval of one half-wavelength W/2. The time intervals W/2 are of course in reality significantly smaller than the intervals T1, T2, T3, etc., which are shown here following one another in quick succession just to provide a simpler illustration. It is apparent that a positive value 14, 17, 18 and a negative value 15, 16, 19 always occur as deviations from the mean value. If the respective measured values of a pair of values are now multiplied, the result will always be a negative value. The mathematical correlation therefore lies in firstly forming, at least approximately, the mean value of all pairs of values, then multiplying the respective deviations from the mean value of a pair of values and subsequently averaging these for each spinning station.

This mathematical correlation is derived from the known autocorrelation theory. It is usually represented by time functions in the literature. The formula for the autocorrelation is generally as follows:

$$K(\Gamma) = \frac{1}{T} \int_0^T f(t) \cdot f(t + \Gamma) \cdot dt$$

where $K(\Gamma)$=correlation factor
f(t)=given function (time function)
$\Gamma$=parameter (a fixed time in the case of a time function)
T=total measurement time.

In our case there is no time function f(t), this being replaced by a yarn cross section trend. Here the autocorrelation calculation is not appropriate to the entire yarn cross section, only to the fluctuations in the yarn cross section, i.e. the deviations from the mean value. (Moreover, just one single value is calculated as a parameter, as in our example the only one which is of interest is that which corresponds to half the cylinder circumference and/or an integer multiple thereof).

In contrast to the above hypothetical case, a defect-free yarn just exhibits purely random fluctuations. If such a yarn is subjected to the same process, the result will be the value zero.

If a yarn comprises both defective periodic and purely random fluctuations, the two above-mentioned cases will be superimposed. According to the intensity of the periodic fluctuation, a more or less negative deviation of the values with respect to the values of the yarns without this defective periodic fluctuation is obtained. This deviation indicates the intensity of the periodic fluctuation, so that the mavericks can be detected.

The traveling sensor 1, which is reciprocated periodically on the bar 4 in a manner known per se, records a pair of values from each spinning station 6, 7, 8, etc. upon each pass. These values are averaged and the deviations from the mean value of each pair of values multiplied and stored electronically in a known manner. The number of passes of the traveling sensor each day is in practice approximately 1000, i.e. 1000 pairs of values from each spinning station.

The mathematical correlation can now be carried out according to the following formula:

$$K(W/2) = \frac{1}{n} \sum_{i=0}^{i=n} (a_j - \overline{a})(b_j - \overline{b})$$

where $K(U/2)$=correlation factor
$a_j$=respective measured value from sensor a
$b_j$=respective measured value from sensor b
$\overline{a}$=mean value of all values a
$\overline{b}$=mean value of all values b
n=number of measured value pairs.

The time parameter ($\Gamma$) in the general formula is here given by the spacing of the measuring members, i.e. corresponding to half the circumference of the front cylinder (U/2). For the above example this means that $a_j$ and $b_j$ are values which have a time lag of half the cylinder circumference.

Defective yarns produce values which deviate in the negative direction from the value of the defect-free yarns according to the intensity of the defect. The traveling sensor covers all or almost all spinning stations. Those spinning stations which exhibit values with the greatest deviations in the negative direction are the mavericks.

Although pairs of values are only obtained from each spinning station as samples, any periodicities can be detected with a sufficient level of confidence. It thus becomes possible to detect defective spinning stations and take appropriate measures in spinning mills having ten or even a hundred thousand spinning stations.

Figure 3:
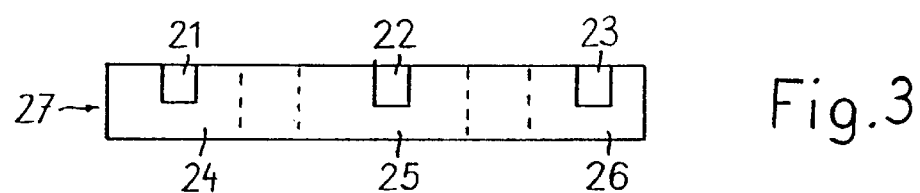
FIG. 3 shows a further construction of a part of the apparatus.

It should also be mentioned that the integer multiples of half the cylinder circumference also indicate the periodicity, with the results deviating towards the negative side in the case of odd multiples and towards the positive side in the case of even multiples. However greater accuracy of the spacing of the two measuring members is necessary here. It is therefore also possible to use more than two measuring members in a traveling sensor in order to increase the level of confidence of the measurement result. They must simply be at the abovementioned spacing of the integer multiple. An arrangement of this kind is illustrated in FIG. 3, which shows three sensors or measuring members 21, 22, 23 which are additionally disposed in a displaceable manner on the traveling sensor 27 in regions 24, 25, 26 defined by broken lines.

If more than just one periodic fluctuation is to be investigated, additional measuring members may be used, in which case their spacing from the first measuring member is to be determined in accordance with the explanations given above.

The entire processing of the measured parameters according to the said formulae is carried out in the evaluation unit 10, which consists of a processor which can be programmed accordingly.

The above method, together with the apparatus, is not restricted to ring spinning machines. It can be applied wherever traveling sensors can be used.

What is claimed is:

1. Method for detecting periodic defects in a test material (12) moved longitudinally, characterized in that at least two measurements of a parameter of the test material which follow one another at a comparatively short interval (W/2) are carried out at time intervals (T1, T2, T3); and in that a mean value is formed from the measurements.

2. Method according to claim 1, wherein said test material is a yarn and the diameter of the yarn is the measured parameter.

3. Method according to claim 1, wherein said test material is a yarn and the mass of the yarn is the measured parameter.

4. Method according to claim 1, characterized in that the measurements are related to the mean value and values (14 to 19) are determined therefrom for deviations.

5. Method according to claim 1, wherein said test material is yarn and the parameters of a plurality of yarns are detected at production stations (6, 7, 8) lying side-by-side in succession.

6. A device for carrying out a method for detecting periodic defects in longitudinally moving test material (12) by carrying out in succession at a comparatively short interval (W/2) at least two measurements of a parameter of the test material at time intervals (T1, T2, T3), said device having at least two sensors (2, 3) which are disposed at a spacing (A) from one another such that they can travel on a track (4) in front of production units (6, 7, 8) of a machine.

7. Apparatus according to claim 6, characterized in that the sensors are connected to an evaluation unit (10).

8. Apparatus according to claim 6, characterized in that the sensors (21, 22, 23) are disposed in a displaceable manner.

* * * * *